US008480728B2

(12) United States Patent
Gregorich et al.

(10) Patent No.: US 8,480,728 B2
(45) Date of Patent: Jul. 9, 2013

(54) STENT SIDE BRANCH DEPLOYMENT INITIATION GEOMETRY

(75) Inventors: Daniel Gregorich, St. Louis Park, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 560 days.

(21) Appl. No.: 11/138,196

(22) Filed: May 26, 2005

(65) Prior Publication Data
US 2006/0271160 A1 Nov. 30, 2006

(51) Int. Cl.
*A61F 2/06* (2013.01)

(52) U.S. Cl.
USPC ........................................................ 623/1.15

(58) Field of Classification Search
USPC .................. 623/1.15, 1.16, 1.2, 1.35, 1.14
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,325,826 A | 7/1994 | Vardi et al. | 623/1.35 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,569,295 A * | 10/1996 | Lam | 606/198 |
| 5,591,228 A | 1/1997 | Edoga | 623/1 |
| 5,596,020 A | 1/1997 | Morris | 516/646 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |

(Continued)

FOREIGN PATENT DOCUMENTS

CA 2220864 7/1999
DE 9014845 2/1991

(Continued)

OTHER PUBLICATIONS

US Patent Application 10/705247, Vardi et al., now abandoned.*

(Continued)

*Primary Examiner* — Thomas McEvoy
(74) *Attorney, Agent, or Firm* — Vidas, Arrett & Steinkraus (57) ABSTRACT

A stent may include a side branch cell comprising a plurality of petals. Each petal may comprise struts and turns, and may have a longitudinal axis oriented at an angle to the stent longitudinal axis. Each petal may comprise a plurality of struts and at least one turn. For each petal, the width of a turn may be greater than the width of the struts. Upon expansion of the stent, a petal may deploy outwardly in a stent radial direction beyond an outer diameter of the rest of the stent.

25 Claims, 4 Drawing Sheets

U.S. PATENT DOCUMENTS

| | | | |
|---|---|---|---|
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,922,021 A | 7/1999 | Jang | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,123,721 A | 9/2000 | Jang | 623/1.6 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,203,569 B1 | 3/2001 | Wijay | |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,245,102 B1 * | 6/2001 | Jayaraman | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,822 B1 | 12/2001 | Vardi et al. | 623/1.35 |
| 6,325,825 B1 * | 12/2001 | Kula et al. | 623/1.3 |
| 6,325,826 B1 | 12/2001 | Vardi | 623/1 |
| 6,334,864 B1 | 1/2002 | Amplatz et al. | 606/200 |
| 6,334,870 B1 | 1/2002 | Ehr | 623/1.5 |
| 6,346,089 B1 | 2/2002 | Dibie | 603/1.15 |
| 6,348,065 B1 | 2/2002 | Brown | 623/1 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,478,816 B1 | 11/2002 | Kveen et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,697 B1 * | 5/2005 | Yip et al. | 623/1.15 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 7,513,907 B2 * | 4/2009 | Lau et al. | 623/1.15 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereume et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0055770 A1 * | 5/2002 | Doran et al. | 623/1.15 |
| 2002/0072790 A1 | 6/2002 | McGuckin, Jr. et al. | 623/1.12 |
| 2002/0111675 A1 | 8/2002 | Wilson | 623/1.35 |
| 2002/0116049 A1 * | 8/2002 | Girton et al. | 623/1.15 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |

| | | | | | |
|---|---|---|---|---|---|
| 2003/0195606 | A1 | 10/2003 | Davidson et al. ............ 623/1.11 | WO | 97/26936 | 7/1997 |
| 2004/0006381 | A1 | 1/2004 | Sequin et al. ................ 623/1.12 | WO | 97/41803 | 11/1997 |
| 2004/0015227 | A1 | 1/2004 | Vardi et al. .................. 623/1.16 | WO | 97/45073 | 12/1997 |
| 2004/0044396 | A1 | 3/2004 | Clerc et al. .................. 623/1.13 | WO | 97/46174 | 12/1997 |
| 2004/0059406 | A1 | 3/2004 | Cully et al. .................. 623/1.11 | WO | 98/19628 | 5/1998 |
| 2004/0088007 | A1 | 5/2004 | Eidenschink .................... 607/1 | WO | 98/36709 | 8/1998 |
| 2004/0102836 | A1 | 5/2004 | Fischell et al. ............... 523/1.15 | WO | 98/37833 | 9/1998 |
| 2004/0117003 | A1 | 6/2004 | Ouriel et al. ................. 623/1.35 | WO | 98/47447 | 10/1998 |
| 2004/0133268 | A1 | 7/2004 | Davidson et al. ............ 623/1.35 | WO | 98/48879 | 11/1998 |
| 2004/0138732 | A1 | 7/2004 | Suhr et al. .................... 623/1.11 | WO | 99/03426 | 1/1999 |
| 2004/0138737 | A1 | 7/2004 | Davidson et al. ............ 623/1.35 | WO | 99/04726 | 2/1999 |
| 2004/0148006 | A1 | 7/2004 | Davidson et al. ............ 623/1.11 | WO | 99/15103 | 4/1999 |
| 2004/0172121 | A1 | 9/2004 | Eidenschink et al. ....... 623/1.11 | WO | 99/15109 | 4/1999 |
| 2004/0186560 | A1 | 9/2004 | Alt ................ 623/1.35 | WO | 99/24104 | 5/1999 |
| 2004/0225345 | A1 | 11/2004 | Fischell et al. ............... 623/1.11 | WO | 99/34749 | 7/1999 |
| 2004/0267352 | A1 | 12/2004 | Davidson et al. ............ 623/1.15 | WO | 99/36002 | 7/1999 |
| 2005/0004656 | A1 | 1/2005 | Das ............................. 623/1.16 | WO | 99/36015 | 7/1999 |
| 2005/0010278 | A1 | 1/2005 | Vardi et al. .................. 623/1.35 | WO | 99/44539 | 9/1999 |
| 2005/0015108 | A1 | 1/2005 | Williams et al. ............. 606/194 | WO | 99/56661 | 11/1999 |
| 2005/0015135 | A1 | 1/2005 | Shanley ....................... 623/1.11 | WO | 99/65419 | 12/1999 |
| 2005/0060027 | A1 | 3/2005 | Khenansho et al. ......... 623/1.35 | WO | 00/07523 | 2/2000 |
| 2005/0096726 | A1 | 5/2005 | Sequin et al. ................ 623/1.12 | WO | 00/10489 | 3/2000 |
| 2005/0102021 | A1 | 5/2005 | Osborne ...................... 623/1.13 | WO | 00/16719 | 3/2000 |
| 2005/0102023 | A1 | 5/2005 | Yadin et al. .................. 623/1.15 | WO | 00/27307 | 5/2000 |
| 2005/0119731 | A1 | 6/2005 | Brucker et al. ............... 623/1.35 | WO | 00/27463 | 5/2000 |
| 2005/0125076 | A1 | 6/2005 | Ginn .......................... 623/23.65 | WO | 00/28922 | 5/2000 |
| 2005/0131526 | A1 | 6/2005 | Wong ........................... 623/1.15 | WO | 01/45594 | 6/2000 |
| 2005/0149161 | A1 | 7/2005 | Eidenschink et al. ....... 623/1.11 | WO | WO 00/30563 * | 6/2000 |
| 2005/0154442 | A1 | 7/2005 | Eidenschink et al. ....... 623/1.11 | WO | 00/44307 | 8/2000 |
| 2005/0154444 | A1 | 7/2005 | Quadri | WO | 00/44309 | 8/2000 |
| 2005/0183259 | A1 | 8/2005 | Eidenschink et al. .......... 29/508 | WO | 00/47134 | 8/2000 |
| 2005/0209673 | A1 | 9/2005 | Shaked ........................ 623/1.11 | WO | 00/48531 | 8/2000 |
| 2005/0228483 | A1 | 10/2005 | Kaplan et al. ................ 623/1.15 | WO | 00/49951 | 8/2000 |
| 2006/0036315 | A1 | 2/2006 | Yadin et al. .................. 623/1.35 | WO | 00/51523 | 9/2000 |
| 2006/0041303 | A1 | 2/2006 | Israel ........................... 623/1.11 | WO | 00/57813 | 10/2000 |
| 2006/0079956 | A1 | 4/2006 | Eigler et al. .................. 623/1.35 | WO | 00/67673 | 11/2000 |
| 2006/0173528 | A1 | 8/2006 | Feld et al. .................... 623/1.15 | WO | 00/71054 | 11/2000 |
| 2006/0271161 | A1* | 11/2006 | Meyer et al. ................. 623/1.15 | WO | 00/71055 | 11/2000 |
| 2007/0073376 | A1 | 3/2007 | Krolik et al. ................. 623/1.11 | WO | 00/74595 | 12/2000 |

FOREIGN PATENT DOCUMENTS

| | | |
|---|---|---|
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, "Kissing" Stent for Bifurcational Coronary Lesion, *Catheterization and Cardiovascular Diagnosis*, vol. 30, pp. 327-330 (Dec. 1993).

Carrie, M.D., Didier, "T"-Shaped Stent Placement: A Technique for the Treatment of Dissected Bifurcation Lesions, *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satter, M.D., Lowell F. "Bifurcation Disease: To Treat or Not to Treat," *Catheterization and Cardiovascular Interventions*, vol. 50, pp. 411-412 (2000).

US. Appl. No. 09/325,996, filed Jun. 4,1999, Vardi et al.

U.S. Appl. No. 09/614,472, filed Jul. 7, 2000, Davidson et al.

U.S. Appl. No. 09/663,111, filed Sep. 15, 2000, Davidson et al.

\* cited by examiner

STENT SIDE BRANCH DEPLOYMENT INITIATION GEOMETRY

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

Stents and bifurcated stents are generally known. When treating a bifurcated vessel, it may desirable to use a stent having a side branch opening configured to provide fluid communication between the primary vessel and a secondary or branch vessel of the bifurcation. A secondary or branch stent may be received within and/or be positioned adjacent to the side branch opening of the primary stent.

A side opening in some stents may further include a structural component, which when deployed, extends from the primary stent and into the branch vessel. In some instances a side branch structure (e.g. limb, arm, branch, etc.) exhibits expansion characteristics that are different from other portions of the primary stent. In some instances, it may be difficult to initiate an outward expansion of the side branch structure.

There remains a need for a stent having a side branch structure which exhibits superior expansion characteristics.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of interconnected strut members. A portion of the interconnected strut members comprise a plurality of petals arranged to define a side branch cell. A first petal comprises a petal strut and a turn. The petal strut has a strut width, and the turn has a turn width. In some embodiments, the turn width may be greater than the strut width.

In at least one embodiment, a stent has an unexpanded state and an expanded state. The stent generally defines a substantially cylindrical wall portion in both the unexpanded and expanded states. The stent includes a side branch cell comprising a plurality of petals. When the stent is expanded from the unexpanded state to the expanded state, a first petal desirably deploys outwardly in a stent radial direction beyond the outer diameter of the substantially cylindrical wall portion.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated. Use of the term "parallel" is intended to describe an orientation in which two elements may be exactly parallel or substantially parallel to one another.

The stent patterns depicted herein are generally shown and described as flat patterns. A person of ordinary skill in the art will understand that a cylindrical stent may be manufactured according to the design of the flat patterns disclosed, and that the stent elements defined by the patterns may form a cylindrical stent wall portion.

Some examples of stent patterns which may be suitable for use in various embodiments of the invention are described in U.S. Pat. No. 5,922,021, U.S. Pat. No. 6,123,721, U.S. Pat. No. 6,334,870, U.S. Pat. No. 6,478,816, U.S. Pat. No. 6,348,065 and U.S. Pat. No. 6,325,826, the entire content of which are hereby incorporated herein by reference in their entireties.

Some examples of stents having a side opening and methods of deploying such stents are disclosed in U.S. Pat. No. 5,596,020 and U.S. Pat. No. 6,835,203, the entire disclosures of which are hereby incorporated herein in their entireties.

Figure 1:
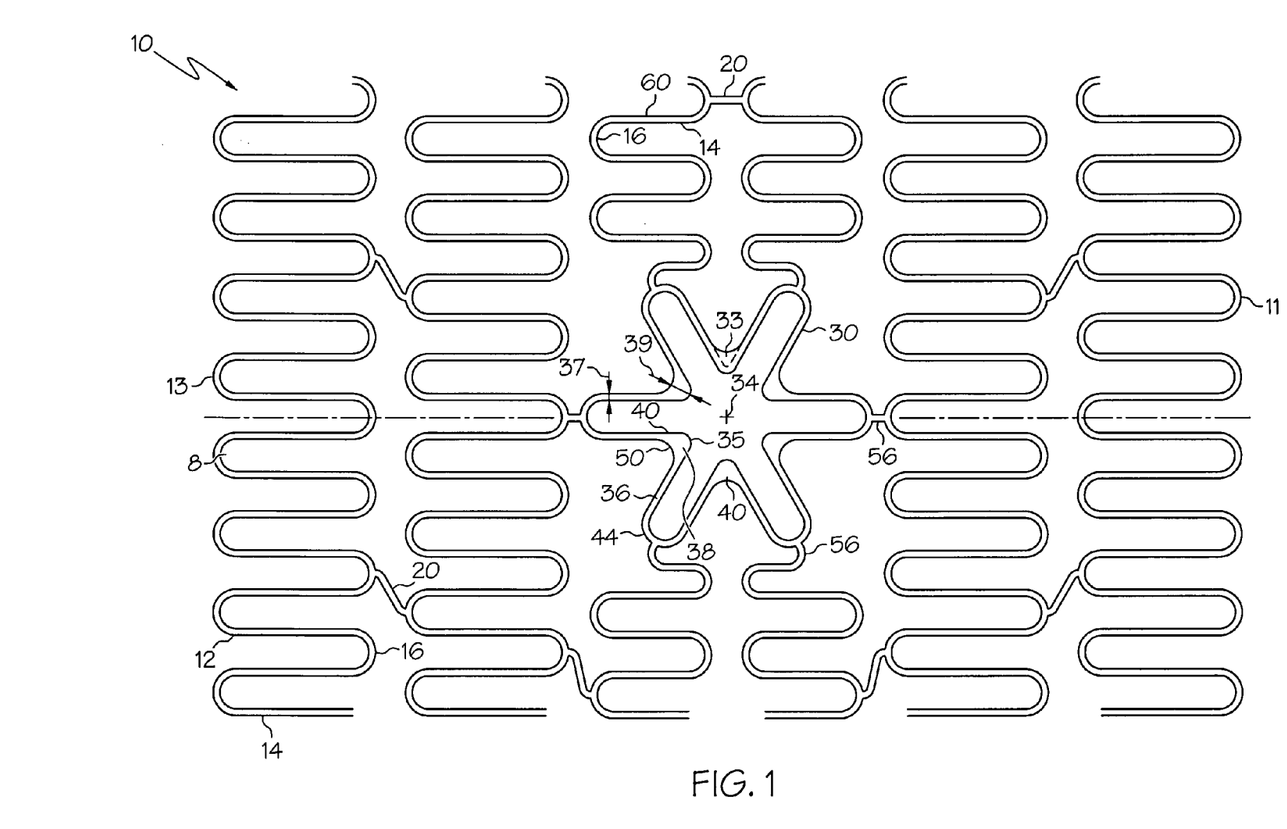
FIG. 1 shows an embodiment of a stent having a side branch cell.

FIG. 1 shows a flat pattern for an embodiment of a stent 10 which may include a side branch cell 30. The stent 10 may comprise a proximal end 11 and a distal end 13. The stent 10 may further comprise a plurality of serpentine bands 12 which may have any suitable shape, and in some embodiments may comprise a plurality of struts 14 connected by turns 16. Adjacent serpentine bands 12 may be connected by connectors 20. The interconnected stent elements, such as struts 14, turns 16 and connectors 20, may define a stent wall portion and may further define a plurality of cells 8. Each cell 8 may comprise an aperture or void in the stent wall portion.

A side branch ring or cell 30 may comprise a continuous strut member, or in some embodiments a plurality of strut members, which may extend in a generally serpentine fashion about the center 34 of the side branch cell 30. While "serpentine" may be used describe most embodiments, the term is not intended to limit the invention. A side branch cell 30 may have any suitable size, shape and configuration of struts.

In some embodiments, the side branch cell 30 may define a plurality of side branch petals 40 which may have any suitable shape and may each be oriented in any suitable direction. A side branch cell 30 may be different than any other cell 8 of the stent 10. For example, a side branch cell 30 may be shaped differently, may have a larger or smaller area, and/or may extend about the circumference or along the length of the stent 10 to a greater or lesser extent than any other cell 8 included in the stent 10.

Each petal 40 may comprise a plurality of struts 36 and at least one turn 38. A strut 36 may be straight along its length, and may be oriented in any suitable direction. A turn 38 may be oriented in any suitable direction and in some embodiments may be oriented toward the center 34 of the side branch cell 30. Petals 40 which are adjacent to one another about the side branch cell 30 may be connected to one another by a connecting portion 44.

Each strut 36 may have a strut width 37. In some embodiments, multiple struts 36 within a petal 40 may have the same strut width 37. In some embodiments, individual struts 36 may have a varying width 37 along their length.

Each turn 38 may have a turn width 39. Each turn 38 may include a front side which may have a peak 35. Each turn 38 may have a back side 50 opposite the front side. A back side 50 may have a straight edge or may have curvature.

In some embodiments, within a petal 40, the strut width 37 of a strut 36 may be less than the turn width 39 of a turn 39. Measurement of the strut width 37 may be taken at a location on the strut 36 immediately adjacent to the turn 38.

Each turn 38 may have a turn width 39 to strut width 37 ratio. In some embodiments, a turn width:strut width ratio may range from 1:1 to 4:1 or greater. In some embodiments, a turn width:strut width ratio may be 1.5:1, 2:1, 2.5:1, 3:1, 3.5:1, etc. In some embodiments, a turn 38 may comprise a continuous piece of material across its turn width 39. In some embodiments, a turn 38 may further comprise a reinforcing material 33 which may be shaped to increase the turn width 39 of a turn 38.

Figure 2:
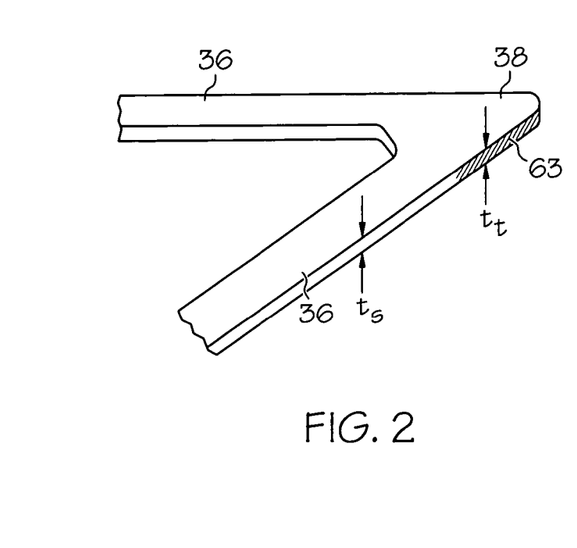
FIGS. 2 and 3 show an embodiment of a petal during stent expansion.
Figure 3:
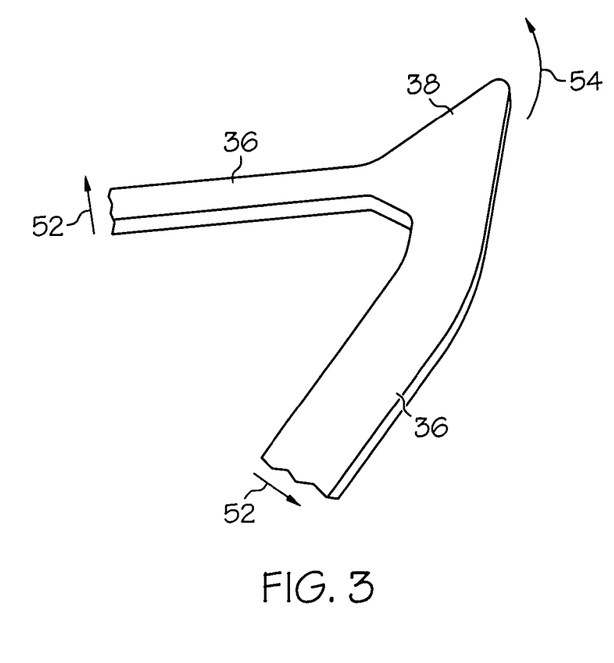

FIGS. 2 and 3 show an embodiment of a petal 40 before and during expansion of a stent 10. FIG. 2 shows a petal 40 according to a nominal or unexpanded state. As the stent 10 is expanded, wherein the diameter of the stent 10 is increased and the size of a side branch cell 30 is increased, struts 36 of a petal 40 may move 52 away from one another as shown in FIG. 3. The outward movement of the struts 36 may cause the turn 38 to buckle outwardly or begin outward deployment 54 in a stent radial direction.

While struts 14 of the serpentine bands 12 may generally remain within the bounds of the cylindrical wall portion of the stent 10 during and after expansion, the petals 40 may deploy outwardly beyond the outer diameter of the cylindrical wall.

Thus, a stent 10 having a side branch cell 30 may be delivered to a deployment site in an unexpanded state. The stent 10 may be properly positioned and expanded. As the side branch cell 30 expands, each petal 40 having a turn width 39 which is greater than a strut width 37 may begin outward deployment 54 substantially in a stent radial direction. The shape of the struts 36 and turns 38 of the petals 40 cause an outward lifting or partial deployment of the petals 40 as the stent is increased in diameter. In some embodiments, when the stent reaches an expanded diameter, the petals 40 of a side branch cell 30 may be fully or at least partially outwardly deployed. Where the petals 40 may become partially deployed, an expansion mechanism such as an inflation balloon may be positioned to fully deploy the petals 40. Examples of some expansion mechanisms are disclosed in U.S. Pat. No. 6,596,020 and U.S. Pat. No. 6,835,203.

In some embodiments, the thickness of a petal 40 may be varied to encourage petal 40 deployment as the stent expands. A strut 36 may have a strut thickness $t_s$. A turn 38 may have a turn thickness $t_t$. When the turn thickness $t_t$ is less than the strut thickness $t_s$ in a petal 40, the petal 40 is more likely to begin an outward deployment upon expansion of the stent.

The thickness of stent elements may be varied according to any suitable method. In some embodiments, the thickness of a portion of a petal 40, such as a turn 38, may be reduced by selectively removing a portion of the material, such as any suitable portion of the shaded region 63 of FIG. 2, for example by brushing, polishing, EDM machining, chemical processing, or any other suitable method.

Referring again to FIG. 1, the stent 10 may include serpentine bands 12 which extend about an entire circumference of the stent 10. In some embodiments, serpentine bands 12 may be located in portions of stent length that do not include a side branch cell 30. In portions of length that do include a side branch cell 30, the stent 10 may include one or more partial serpentine bands 60, which may extend from one side of a side branch cell 30 about the circumference of the stent 10 to the other side of the side branch cell 30. The design of struts 14 and turns 16 in a partial serpentine band 60 may be similar to or different than the design geometry of the standard serpentine bands 12.

A stent 10 may include side branch connectors 56 which may connect between the side branch cell 30 and other portions of the stent 10. A side branch connector 56 may extend from any portion of a side branch cell 30, such as a petal 40 or connecting portion 44, and connect to any other portion of the stent 10, such as a serpentine band 12 or a partial serpentine band 60.

In some embodiments, a side branch connector 56 may include straight portions, peaks, valleys or other undulations. In some embodiments, a side branch connector 56 may comprise a flexible connector which may support an ostium when deployed in a vessel.

Figure 4:
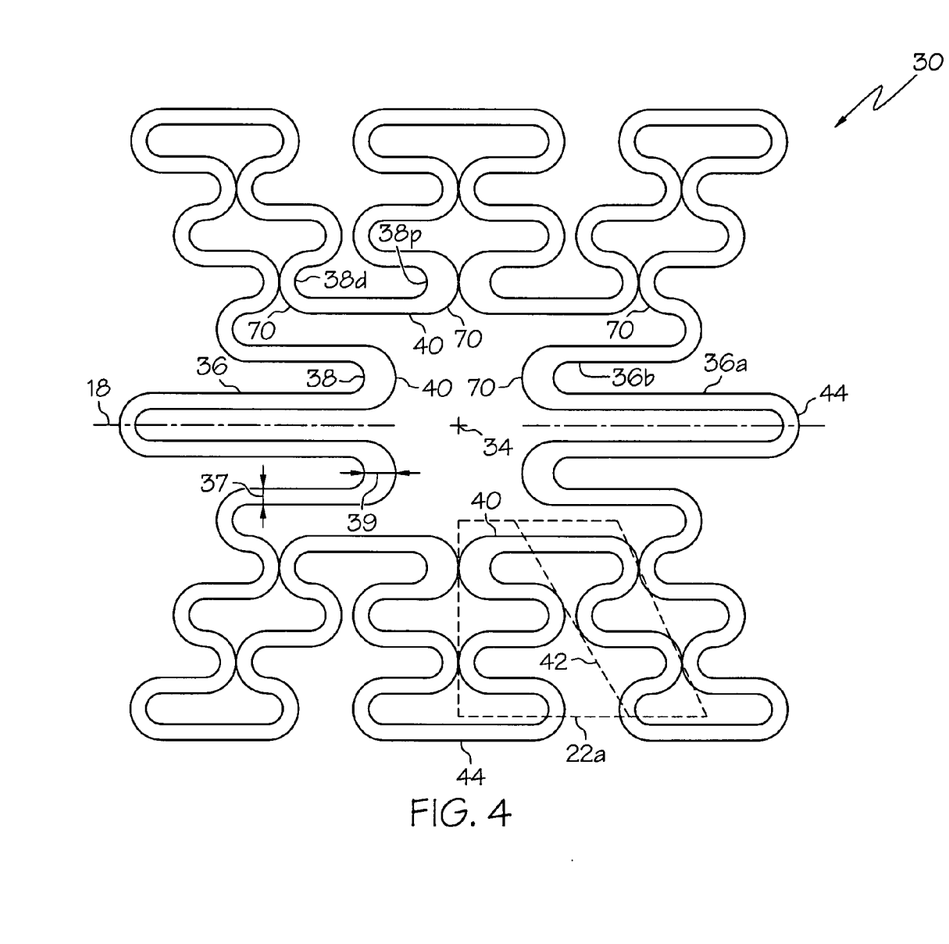
FIG. 4 shows another embodiment of a side branch cell.

FIG. 4 shows another embodiment of a side branch cell 30 which may comprise a plurality of petals 40. Each petal 40 may have an approximate longitudinal axis 42. In some embodiments, a petal 40 may have a longitudinal axis 42 which is oriented to extend substantially radially outwardly from the center 34 of the side branch cell 30. A longitudinal axis 42 may pass through the centroid of the stent elements which comprise the petal 40. A reference box 22a is drawn about a portion of the side branch cell 30 which may be defined as a petal 40.

Each petal 40 may comprise a plurality of struts 36 and at least one turn 38. A strut 36 may be straight along its length, and may be oriented in any suitable direction. A turn 38 may be oriented in any suitable direction. In some embodiments, a turn 38 may comprise a proximal turn 38p oriented with a peak facing the proximal end 11 (see FIG. 1) of the stent 10, or a distal turn 38d oriented with a peak facing the distal end 13 (see FIG. 1) of the stent 10. Petals 40 which are adjacent to one another about the side branch cell 30 may be connected to one another by a connecting portion 44. In various locations, a connecting portion 44 may comprise a turn 38, a strut 36, or any combination of one or more turns 38 and one or more struts 36.

A petal 40 may include struts 36 that are oriented parallel to the longitudinal axis 18 of the stent 10. In some embodiments, a majority of the struts 36 or all of the struts 36 in a petal 40 may be oriented parallel to the longitudinal axis 18 of the stent 10. This may be true even though the longitudinal axis 42 of the petal 40 may be oriented at an angle with respect to the longitudinal axis 18 of the stent 10. In some embodiments, one or more struts 36 may be oriented at approximately 30° to 60° with respect to the longitudinal axis 18 of the stent 10. In some embodiments, one or more struts 36 may be oriented at approximately 45° with respect to the longitudinal axis 18 of the stent 10 (see FIG. 5).

Each petal 40 may further comprise one or more appendages 70. An appendage 70 may comprise a first strut 36a and a second strut 36b connected by a turn 38. In some embodiments, an appendage 70 may include a proximal turn 38p, or may include a distal turn 38d. An appendage 70 may have an approximate longitudinal axis 72, and the approximate longitudinal axis 72 may be parallel to the longitudinal axis 18 of the stent 10.

In some embodiments, one or more petals 40 may comprise a plurality of appendages 70. A single petal 40 may include appendages 70 that are oriented in similar directions, in different directions or in opposite directions. A single petal 40 may include at least one appendage 70 having a proximal turn 38p, and at least one other appendage 70 having a distal turn 38d.

Each strut 36 may have a strut width 37. In some embodiments, multiple struts 36 within a petal 40 may have the same strut width 37. In some embodiments, individual struts 36 may have a varying width 37 along their length.

Each turn 38 may have a turn width 39. In some embodiments, within a petal 40, the strut width 37 of a strut 36 may be less than the turn width 39 of a turn 38. Measurement of the strut width 37 may be taken at a location on the strut 36 immediately adjacent to the turn 38. In some embodiments, a petal 40 may include a plurality of turns 38, and some turns 38 may have a greater turn width 39 than other turns 38 of the petal 40. In some embodiments, the turn 38 of a petal 40 which has the greatest turn width 39 may be located closer to the center 34 of the side branch cell 30 than other turns 38 of the petal 40. In some embodiments, the turn width 39 may progressively decrease as the distance from the center 34 of the side branch cell 30 to the turn 38 increases.

In some embodiments, a turn width:strut width ratio may range from 1:1 to 4:1 or more as herein described. As the side branch cell 30 expands, each petal 40 having a turn width 39 which is greater than a strut width 37 may inherently begin outward deployment 54 substantially in a stent radial direction. The shape of the struts 36 and turns 38 of the petals 40 may cause an outward lifting or partial deployment of the petals 40 as the stent is increased in diameter. When the stent reaches an expanded diameter, the petals 40 of a side branch cell 30 may be fully or at least partially outwardly deployed.

In some embodiments, a petal 40 may have multiple turns 38, and the turn thickness $t_t$ of individual turns 38 may vary. In some embodiments, turns 38 which are located closer to the center 34 of the side branch cell 30 may have a larger turn thickness $t_t$ than other turns 38 of the petal 40. In some embodiments, the turn thickness $t_t$ may progressively increase as the distance from the center 34 of the side branch cell 30 to the turn 38 increases.

In some embodiments, the design of a side branch cell 30, and particularly the design of petals 40 having a plurality of struts 36 oriented parallel to the stent longitudinal axis 10, may allow for more struts 14 and turns 16 in a partial serpentine band 60 than prior art designs. The design of a side branch cell 30 may also allow the design of the partial serpentine band(s) 60 to be consistent with the design of the standard serpentine bands 12. This allows the stent to provide more scaffolding support to vessel locations adjacent to the petal 40 region, particularly around juncture points between a main branch vessel and a side branch vessel, such as the carina and vessel areas contralateral to the carina.

Figure 5:
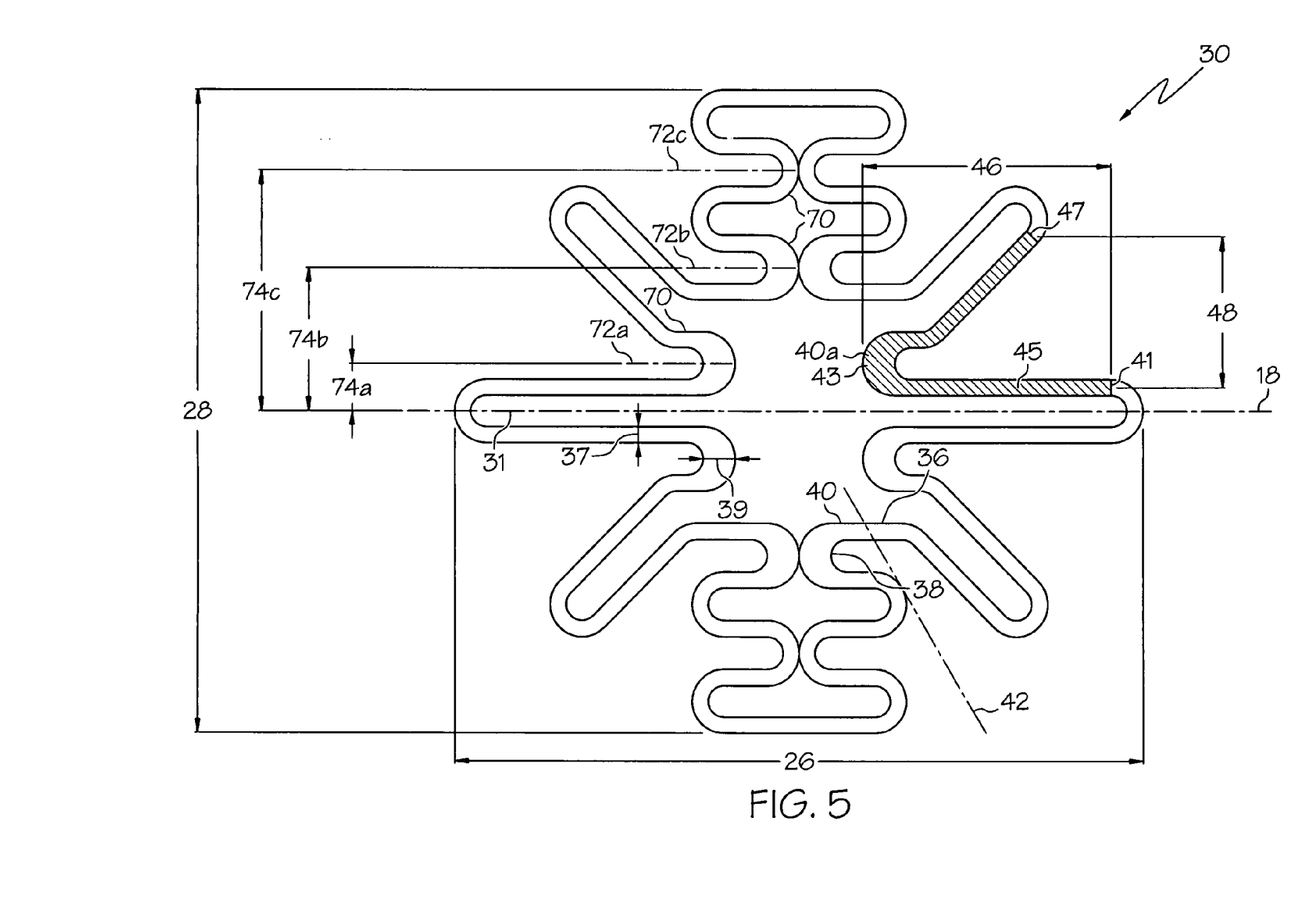
FIG. 5 shows another embodiment of a side branch cell.

FIG. 5 shows another embodiment of a side branch cell 30. Each petal 40 may occupy an area of space on the surface of the stent. For the purposes of the following disclosure, an embodiment of a petal 40a is shown with the approximate bounds of the petal 40a shaded. Each petal 40 may include a longitudinal length component 46 or a distance between a proximal most point (e.g. 41) and a distal most point (e.g. 43) of the petal 40 as measured in a direction parallel to the stent longitudinal axis 18. A proximal most point 41 may be defined as the point of a petal 40 that is closest to the proximal end 11 (see FIG. 1) of the stent, and a distal most point 42 may be defined as the point of a petal 40 that is closest to the distal end 13 (see FIG. 1) of the stent. Although a proximal most point 41 and a distal most point 43 are specifically indicated in FIG. 5 with respect to petal 40a, the location of a proximal most point and the location of a distal most point on any petal 40 may change as the shape of any petal 40 may change with stent crimping and/or stent expansion.

Each petal 40 may further include a circumferential length component 48, or a distance between opposed circumferential extremities 45, 47 of a petal 40 as measured in a direction about the circumference of the stent 10. As with the proximal most and distal most points 41, 43 of a petal 40, the locations of points which comprise the opposed circumferential extremities 45, 47 for a given petal 40 may change with stent crimping and/or stent expansion. The circumferential length component 48 of a petal 40 may be perpendicular to the longitudinal length component 46 of the petal 40.

Similar to the circumferential length component 48 and longitudinal length component 46 of a petal 40, a side branch cell 30 may include a longitudinal length component 26, or a distance between proximal most and distal most points of the side branch cell 30 as measured parallel to the stent longitudinal axis 18. A side branch cell 30 may also include a circumferential length component 28, or a distance between opposed extremities of the side branch cell 30 as measured in a direction about the circumference of the stent 10. The locations of a proximal most point, a distal most point, and the opposed circumferential extremities may change as a side branch cell 30 may change in size and shape with stent crimping and/or stent expansion. The longitudinal length component 26 of the side branch cell 30 may be perpendicular to the circumferential length component 28.

The geometric design of various embodiments of a side branch cell 30, including the design of the individual petals 40 within a side branch cell 30, may allow a stent 10 to expand more similarly to a standard stent not having a side branch cell 30. Desirably, upon expansion, the circumferential length component 28, 48 of a petal 40 or a side branch cell 30 may experience an increase that is proportionally larger than any related increase in the longitudinal length component 26, 46 of the respective petal 40 or side branch cell 30. In some embodiments, a longitudinal length component 26, 46 may remain the same or even reduce as the stent 10 expands. The geometric design of the petals 40, and particularly the petals 40 which have an approximate longitudinal axis 42 that is nonparallel to the stent longitudinal axis 18 and a plurality of struts 36 which are oriented parallel to the stent longitudinal axis 18, allows for a relatively large increase in the circumferential length component 28, 48 as compared to any change (i.e. increase or decrease) in the longitudinal length component 26, 46 of the petal 40 or side branch cell 30 during stent expansion.

As a stent expands, the petals 40 may change shape, and the orientation of struts 36 and turns 38 may also change. Struts 36 which are parallel to the stent longitudinal axis 18 in an unexpanded state may reorient on expansion and be nonparallel to the stent longitudinal axis 18 when the stent is expanded.

Appendages 70 may also change shape as the stent expands. In some embodiments, although an appendage 70 may change shape, the approximate longitudinal axis 72 of the appendage 70 may remain parallel to the stent longitudinal axis 18 after expansion.

An appendage 70 may have a longitudinal axis 72 which is a predetermined distance away from a longitudinal axis 31 of the side branch cell 30, as measured in a stent circumferential direction. FIG. 5 shows a first longitudinal axis 72a, a second longitudinal axis 72b and a third longitudinal axis 72c for three respective appendages 70. Three respective predetermined distances 74a, 74b, 74c are shown between the side branch cell longitudinal axis 31 and the respective appendage longitudinal axes 72a, 72b, 72c.

As the stent expands, each appendage longitudinal axis 72 may displace away from the side branch cell longitudinal axis 31. The greater the distance 74 between the appendage longitudinal axis 72 and the side branch cell longitudinal axis 31, the greater the increase in the distance 74 may be. For example, during expansion, appendage longitudinal axis 72a may displace away from the side branch cell longitudinal axis 31. Appendage longitudinal axis 72b may also displace away from the side branch cell longitudinal axis 31. The amount of displacement of appendage longitudinal axis 72b may be greater than the amount of displacement of appendage longitudinal axis 72a. Similarly, appendage longitudinal axis 72c may also displace away from the side branch cell longitudinal axis 31, and the amount of displacement of appendage longitudinal axis 72c may be greater than the amount of displacement of appendage longitudinal axis 72b.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, a stent delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments, at least a portion of the stent is configured to include one or more mechanisms for the delivery of a therapeutic agent. Often the agent will be in the form of a coating or other layer (or layers) of material placed on a surface region of the stent, which is adapted to be released at the site of stent implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly-dependent claim format which creates a dependency from a prior antecedent-possessing claim other than the specific claim listed in such dependent claim below.

This completes the description of some of the various embodiments of the invention. Those skilled in the art may recognize other equivalents to the specific embodiment described herein which equivalents are intended to be encompassed by the claims attached hereto.

The invention claimed is:

1. A stent comprising a plurality of interconnected strut members defining a plurality of cells, a plurality of said interconnected strut members comprising a side branch ring comprising a plurality of petals and connecting portions, adjacent petals connected by a connecting portion, the side branch ring defining a side branch cell having a center point, the side branch cell being shaped differently than other cells of the stent, each of said petals defining a petal longitudinal axis, each petal longitudinal axis extending substantially radially outward from said center point, said petals including at least three first petals, each first petal comprising a petal strut and a turn, said petal strut having a strut width, said turn having a turn width, a connecting portion attached to said petal strut having a connecting portion width, wherein the turn width is greater than the strut width, the turn width is greater than the connecting portion width and the turn only connects to portions of the side branch ring.

2. The stent of claim 1, wherein said turn comprises a continuous piece of material from a peak of the turn to a back side of the turn.

3. The stent of claim 1, wherein said turn includes a back side, the back side having curvature.

4. The stent of claim 1, wherein each of said turns of said at least three first petals is a first turn, each first petal comprises a plurality of struts and a plurality of turns including said first turn and a second turn, the first turn located closer to the center point of the side branch cell than the second turn, a turn width of the first turn being greater than a turn width of the second turn.

5. The stent of claim 4, wherein at least one first petal comprises a plurality of struts which are oriented substantially parallel to a longitudinal axis of the stent.

6. The stent of claim 4, wherein at least one first turn faces a proximal end of the stent.

7. The stent of claim 4, wherein at least one first petal defines a longitudinal axis that is non-parallel to a stent longitudinal axis when the stent is unexpanded.

8. The stent of claim 1, wherein each petal comprises a petal strut having a strut width and a turn having a turn width, wherein the turn width is greater than the strut width in each petal.

9. The stent of claim 1, wherein each petal further comprises a plurality of turns, each turn having a turn width, wherein for each petal, the turn having the greatest turn width is located closer to the center point of the side branch cell than other turns of the petal.

10. The stent of claim 1, wherein said turn width is at least 1.5 times greater than said strut width.

11. The stent of claim 1, wherein at least one first petal includes a petal longitudinal axis that is nonparallel to a stent longitudinal axis when the stent is unexpanded.

12. The stent of claim 1, wherein at least one first petal has a constant thickness.

13. The stent of claim 1, wherein at least one first petal includes a strut thickness and a turn thickness, the turn thickness being less than the strut thickness.

14. The stent of claim 13, wherein at least one first petal comprises a first turn and a second turn, the second turn having a turn thickness that is greater than the turn thickness of the first turn.

15. The stent of claim 14, wherein the first turn is located closer to the center point of the side branch cell than the second turn.

16. The stent of claim 1, wherein at least one first petal comprises at least three struts that are oriented parallel to a longitudinal axis of the stent.

17. The stent of claim 1, wherein at least one first petal comprises a first strut and a second strut that are oriented parallel to a longitudinal axis of the stent, the first strut being longer than the second strut.

18. A stent having an unexpanded state and an expanded state, the stent generally defining a substantially cylindrical wall portion in the unexpanded state, the stent comprising a framework defining a plurality of cells, a side branch cell defined by at least three petals including a first petal, the side branch cell being shaped differently than other cells of the stent and defining a side branch center point, each of said petals defining a longitudinal axis, each longitudinal axis extending substantially radially outward from said center point, the first petal comprising a first strut, a turn, a second strut and a third strut, the first, second and third struts bounding the side branch cell, said longitudinal axis of said first petal oriented in a side branch radial direction and being nonparallel to a stent longitudinal axis when the stent is in the unexpanded state, wherein when the stent is expanded from the unexpanded state to the expanded state, a portion of the first strut moves away from a portion of the second strut, and the turn buckles outwardly in a stent radial direction beyond an outer diameter of said substantially cylindrical wall portion.

19. The stent of claim 18, wherein said first petal lies within the bounds of said substantially cylindrical wall portion in the unexpanded state.

20. The stent of claim 18, wherein each petal buckles outwardly beyond an outer diameter of said substantially cylindrical wall portion when the stent is in the expanded state.

21. The stent of claim 18, wherein said struts comprise a strut having a strut width and said turn has a turn width, wherein the strut width is less than the turn width.

22. The stent of claim 21, wherein a thickness of the turn is less than a thickness of the strut having said strut width.

23. The stent of claim 21, wherein the turn has an equal thickness as the strut having said strut width.

24. The stent of claim 18, wherein the said first, second and third struts are each oriented parallel to a longitudinal axis of the stent.

25. The stent of claim 18, wherein the first strut is longer than the second strut.

\* \* \* \* \*